(12) United States Patent
del Soldato

(10) Patent No.: US 7,087,588 B2
(45) Date of Patent: Aug. 8, 2006

(54) NITRIC OXIDE DONORS CAPABLE OF REDUCING TOXICITY FROM DRUGS

(75) Inventor: Piero del Soldato, Milan (IT)

(73) Assignee: Nicox S.A., Sophia Antipolis (FR)

( * ) Notice: Subject to any disclaimer, the term of this patent is extended or adjusted under 35 U.S.C. 154(b) by 0 days.

(21) Appl. No.: 10/885,121

(22) Filed: Jul. 7, 2004

(65) Prior Publication Data

US 2004/0242651 A1  Dec. 2, 2004

Related U.S. Application Data

(63) Continuation of application No. 09/125,878, filed as application No. PCT/EP97/00873 on Feb. 24, 1997, now abandoned.

(30) Foreign Application Priority Data

Feb. 26, 1996 (IT) ............... MI96A0352

(51) Int. Cl.
*A61K 31/56* (2006.01)
*A61K 31/60* (2006.01)
*A61K 31/70* (2006.01)
*A61K 31/545* (2006.01)
*A61K 47/00* (2006.01)

(52) U.S. Cl. .................. 514/50; 514/165; 514/169; 514/200; 514/788

(58) Field of Classification Search ............ 514/50, 514/165, 200, 169, 788
See application file for complete search history.

(56) References Cited

U.S. PATENT DOCUMENTS

| 5,620,416 A | 4/1997 | Riviere ............ 604/500 |
| 5,703,073 A | 12/1997 | Garvey et al. ........ 514/226.5 |

FOREIGN PATENT DOCUMENTS

| WO | WO 94/04484 | 3/1994 |
| WO | WO 94/12463 | 6/1994 |
| WO | WO 95/09831 | 4/1995 |
| WO | WO 95/26768 | 10/1995 |
| WO | WO 95/30641 | 11/1995 |
| WO | WO-A-96/32946 | 10/1996 |

OTHER PUBLICATIONS

McNaughton, Life Sci, vol. 45, 1869-1876 (1989).
Kitagawa, Pharm Expt Ther 1133-1137 (1990).
Konturek, Europ J Pharmacol 239 215-217 (1993).
Wallace, J. Gastroent Hepatol 9 S40-S44 (1994).
Barrachina, Europ J Pharmacol 281 R3-R4 (1995).
Wallace, Pulmonary-Allergy Dermat., Gastroint. & Arth., Sect. Rev. 9 613-619 (1995).
Johnstone, J Am. College Card. 145A (1989).
Boughton-Smith, Eur J Pharmacol 191 485-488 (1990).
Brown, Eur J Pharmacol 223 103-104 (1992).
Wallace, Gastroenterol. 173-179 (1994).
Wallace, Eur J. Pharmacol 257, 249-255 (1994).
Elliott, Gastroent., 524-530 (1995).
Wallace, J. Clin. Invest. 96, 2711-2718 (1995).
Wallace, Eur J. Pharmacol 280, 63-68 (1995).
Cuzzolin, Pharmacol. Res. 31, 61-65 (1995).
Rivas-Cabanera, Nephron 71, 203-207 (1995).
Lopez-Neblina, Trans Proc vol. 27, 1883-1885 (1995).
Wallace, Novel Molecular Approaches to Anti-Inflammatory Theory, 121-129 (1995).
Vanderford, Clin. Res. 41(2), 1328-1332 (1993).
Nally, Brit. J. Pharmacol. 113, 1328-1332 (1994).
MIMS (monthly index medical supplies), publ date Dec. 27, 1995.
Langford, Arterioscl. Thromb. Vasc. Biol., vol. 16, 1, 51-55 (Jan. 1996).
Gissi-3, Lancet, 343, 1115-1122 (1994).
Dupuis, Can. J. Cardiol., vol. 6, 281-286 (1990).
Raij, Prostaglandins 54, 53-58 (1996).
Bennett, Urol. Clin. N. Amer. 17, 156-156 (1990).
Amore, Kidney Int., 47, 1507-1514 (1995).
Palmer, Nature 333, 664-666 (1988).
Ashab, Kidney Int. 47, 1515-1521 (1995).
Torfgard, Cardiov. Drugs and Ther. 8, 701-717 (1994).

*Primary Examiner*—Elli Peselev
(74) *Attorney, Agent, or Firm*—Arent Fox PLLC

(57) ABSTRACT

Use of organic compounds containing the —$ONO_2$ function, or inorganic compound containing the —NO group or compositions comprising said compounds to reduce the toxicity caused by drugs to the gastrointestinal and/or renal apparatus, said compounds being characterized in that they are nitric oxide NO donors i.e., when they are put into contact in vitro with cells of the vasal endothelium or platelets.

16 Claims, No Drawings

NITRIC OXIDE DONORS CAPABLE OF REDUCING TOXICITY FROM DRUGS

This is a continuation of application Ser. No. 09/125,878 filed Aug. 26, 1998, now abandoned, which is a National Stage Entry of PCT/EP97/00873 filed Feb. 24, 1997. The disclosure of the prior applications is hereby incorporated by reference herein in its entirety.

The present invention relates to the prevention or the reduction of the iatrogenic toxicity. More particularly it relates to the reduction of toxicity caused by drugs at renal and/or gastrointestinal and/or respiratory level.

It is well known that the toxicity from drugs is assuming a more and more important role in human pathology. It suffices to consider the gastropathy caused by anti-inflammatory drugs which implies an yearly cost in the range of some billions of dollars for the U.S. public administration. See for instance Bloom, B. S. Am. J. Medicine 84 (supplement 2A), 20, 1988, which reports the yearly costs for the arthritis treatment in USA amounting to more than 12 billions of dollars, of which more than 30% is attributable to the care of the side effects connected to the anti-inflammatory/antiarthritic pharmacological treatment.

Likewise the nephropathy caused by antibiotics can mean for the single patient losses of thousands of dollars to cover hospitalization expenses. See for instance Berndt W. O. et al. in "Principles of Pharmacology" Munson P. L. Ed. p. 685, 1995.

An object of the present invention consists in compounds capable of reducing the toxicity caused by non nitroderivative drugs to the gastrointestinal and/or renal and/or respiratory apparatus.

It has been surprisingly and unexpectedly found that this is possible if organic compounds containing the —$ONO_2$ function, or inorganic compounds containing the —NO group are employed, said compounds being characterized in that they are nitric oxide NO donors, i.e. when they are put into contact in vitro with cells of the vasal endothelium, platelets, etc., and after incubation of 5 minutes at the temperature of 37° C. are capable of releasing NO and activating the cGMP (Guanosine cyclic 3',5'-(hydrogen phosphate)) synthesis, as determined by the specific tests utilized, which will be described in detail in the examples.

The unexpected and surprising results of the claimed invention are also shown by the following fact: the combination of the nitroderivatives of the invention with a non nitroderivative drug is useful not only to reduce the toxicity of the drug but also to eliminate the disadvantages related to the nitroderivatives administration.

For example nitroglycerin, when given with enalapril to rats, following repeated subcutaneous administration at the dose of 1 mg/kg per day, did not cause any tolerance, differently from nitroglycerin alone.

Therefore the combination of the present invention results in the so called lower tolerance by chronical administration pharmaceutical compositions. This is a great advantage since no problem arises also by taking nitroderivatives for a long time and maintaining the same effectiveness of the nitroderivative compounds.

The organic compounds containing —$ONO_2$ functions which can be mentioned as an example, are the following, which are reported in The Merck Index 11th Ed.—1989 and prepared with the known methods, for instance those reported in the Merck, incorporated herein by reference:

clonitrate (3-chloro-1,2-propanediol dinitrate) (Merck No. 2390) having the formula $C_3H_5ClN_2O_6$ and formula of structure

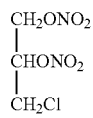

erythrityltetranitrate (1,2,3,4 butanetetroltetranitrate) (Merck No. 3622) having the formula $C_4H_6N_4O_{12}$ and formula of structure

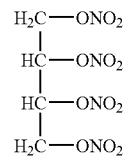

mannitol hexanitrate (Merck No. 5630) having the formula $C_6H_8N_6O_{18}$ and formula of structure

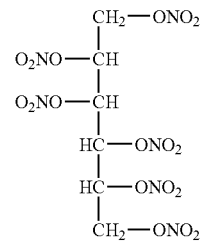

nicorandil (N-[2-(nitrooxy)ethyl]-3-pyridine-carboxamide) (Merck No. 6431) having the formula $C_8H_9N_3O_4$ and formula of structure

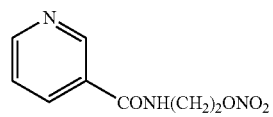

nitroglycerin (1,2,3 propanetriol trinitrate) (Merck No. 6528) having the formula $C_3H_5N_3O_9$ and formula of structure

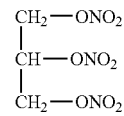

pentaerythritoltetranitrate (2,2-bis [(nitrooxy)-methyl]-1,3-propanedioldinitrate) (Merck No. 7066) having the formula $C_5H_8N_4O_{12}$ and formula of structure

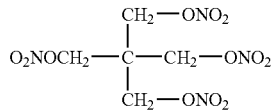

pentrinitrol (2,2-bis[(nitrooxy)methyl]-1,3-propanediol-mononitrate) (Merck No. 7094) having the formula $C_5H_9N_3O_{10}$ and formula of structure

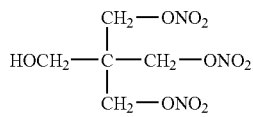

propatylnitrate (2-ethyl-2-[(nitrooxy)methyl]-1,3-propanedioldinitrate) (Merck No. 7821) having the formula $C_6H_{11}N_3O9$ and formula of structure

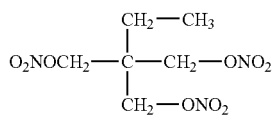

trolnitratephosphate (2,2',2''-nitryltrisethanoltrinitrate phosphate) (salt 1:2) (Merck No. 9682) having the formula $C_6H_{18}N_4O_{17}P_2$ and formula of structure

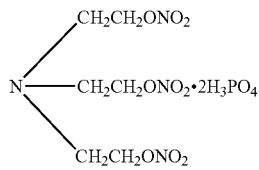

Among the inorganic compounds containing the —NO group, nitroprussiates can be mentioned, such as for instance: sodiumnitroprussiate (pentakis (cyano-C)nitrosyl-ferrate (2-)disodium) (Merck No. 8600) having the formula $Na_2[Fe(CN)_5NO]$.

Other compounds containing the —ONO$_2$ function are reported in patent applications in the name both of the Applicant WO 95/30641; WO 95/09831; WO 94/12463 and of others WO 94/04484. These patent applications PCT/WO are herein incorporated by reference both for the compounds and for the preparation processes.

The nitric oxide NO donors compounds of the invention are indicated hereinafter by the term DON-NO.

Among the drugs not containing nitrodrivative groups causing renal and/or gastrointestinal and/or respiratory toxicity, the following compounds belonging to different therapeutic classes, can be mentioned, as an example:
anti-tumoral drugs among which cisplatin, 5 fluoro-uracil can be mentioned;
immunodepressive drugs among which cyclosporin can be cited;
anti-viral drugs among which acyclovir can be cited;
non-steroidal anti-inflammatory drugs, among which ibuprofen, indomethacin, diclofenac, ketorolac, naproxen, ketoprofen, mefenamic acid, flunixin, flufenamic acid, niflumic acid can be mentioned;
anti-thrombotic drugs among which aspirin can be mentioned;
steroidal anti-inflammatory drugs among which cortisone, dexamethasone, methylprednisolone can be mentioned;
antibiotics among which ciprofloxacin, gentamicine can be mentioned;
inhibitors of the angiotensin-converting enzyme (ACE) among which captopril, enalapril can be mentioned;
beta-adrenergic antagonists, e.g. atenolol, metoprolol, timolol, propanol, etc. Also for these agents respiratory toxicity was reduced by the administration of the nitro-derivatives of the invention.

All these drugs are reported in the Merck Index (see above) herein incorporated by reference.

The preferred compounds as drugs not containing the nitroderivative group of which it is desired to prevent or reduce the toxicity, are antitumoral drugs, in particular cis-platinum (cisplatin); immunodepressive drugs, in particular cyclosporin; steroidal anti-inflammatory drugs, in particular dexamethasone, methylprednisolone; inhibitors of the angio-tensin-converting enzyme (ACE), in particular enalapril, captopril.

The administration of the compounds of the present invention can be carried out by oral, parenteral or transdermic way and they are generally administered simultaneously, successively or previously to the drug not containing the nitroderivative group which causes the gastrointestinal and/or renal and/or respiratory toxicity. The transdermic way is the preferred one and the compounds of the invention are administered under the form of patches or plasters. In particular conventional patches based on nitroglycerine are preferred, according to an embodiment of the present invention.

The dosages are the conventional ones already utilized for the DON-NO for the cardiovascular indications in human therapy. A commercial patch is generally utilized for one day or two days and then replaced. Slow release-patches could be used for more days before being replaced. Sometimes also two patches a day, each for twelve hours, can be utilized. This procedure is generally preferred when a greater effectiveness is required.

Such dosages are preferred since they do not cause significant side effects as those typical of this class of drugs, for instance cephalea, marked hypertension, etc.

The dosage ranges for the human therapy generally vary between 5–15 mg/24 h in 1–2 applications.

The compounds of the invention containing the —ONO$_2$ functions or the —NO group producing the effects of the invention, as already said, must meet the test in vitro defined herein in detail.

In particular the test relates to the generation of nitric oxide from the NO donors of the present invention, among which, for instance, nitroglycerine, nicorandil, nitro-prussiate, etc., when they are put in the presence of endothelial cells (method a), or platelets (method b).

a) Endothelial cells

Cells of the human umbilical vein, spread on the plate, with density of $10^3$ cells/plate were incubated with scalar concentrations of NO donor (1–100 µg/ml) for 5 minutes. The incubation medium (physiologic solvent, for instance Tyrode) was then analyzed to determine the capacity to generate NO, by means of:
1) the determination of nitric oxide by chemiluminescence;
2) the cGMP determination (cyclic GMP No. 2715 of the above mentioned Merck).

As regards the analysis by chemiluminescence, an amount equal to 100 µl was injected in the reaction chamber of a chemiluminescence analyser containing glacial acetic acid and potassium iodide. The nitrites/nitrates present in the medium in these conditions are converted into NO which is then determined after its reaction with ozone, with consequent generation of light. As it usually occurs in the devices measuring chemiluminescence, the produced luminescence is directly proportional to the NO levels generated and can be measured by the suitable photomultiplier unit of a chemiluminescence analyser. The photomultiplier converts the incident light into electric voltage, which is then quantitatively recorded. On the basis of a calibration curve, prepared with scalar concentrations of nitrite, it was possible to determine quantitatively the generated NO concentration. For instance, from the incubation of 100 μmoles of nicorandil, an amount equal to about 10 μmoles of NO was generated.

As regards the cGMP determination, a portion of the incubation medium (equal to 100 μl) was centrifuged at 1000 revolutions for 20 seconds. The supernatant was discharged and the sediment taken again with iced phosphate buffer (pH 7.4). The cGMP levels produced were tested, by specific immuno-enzymatic reactants. From such experiments it resulted that, in these experimental conditions, the incubation with one of the various tested NO donors, caused a significant increase of cGMP with respect to the values obtained in absence of a NO donor. For instance, further to incubation with 100 μmoles of sodium nitroprussiate, an increase of about 20 times the value obtained with the incubation of only the vehicle without the NO donor was recorded.

b) Platelets

Washed human platelets, prepared analogously with what described by Radomski et al, (Br. J. Pharmacol. 92, 639–1987), were utilized. Aliquots of 0.4 ml were incubated with scalar concentrations of NO donors (1–100 μg/ml) for 5 minutes. The incubation medium (f.i. Tyrode) was then analysed to determine the capacity of generating NO, by determination of nitric oxide by chemiluminiscence and cGMP, with the modalities described in the previous paragraph, for the analyses carried out on the endothelial cells. As to the determination by chemiluminescence, also in this case, on the basis of a calibration curve, prepared with scalar concentrations of nitrite, it was possible to determine quantitatively the concentration of generated NO. For instance, after incubation of 100 μmoles of nicorandil, an amount equal to 35 μmoles of NO was generated.

As regards the cGMP determination, also in these experimental conditions, it resulted that the incubation with one of the various No donors tested caused a significant increase of cGMP with respect to the values obtained in absence of a NO donor. For instance, after incubation with 100 μmoles of sodium nitroprussiate, an increase of about 30 times the value obtained with the incubation of only the vehicle without the NO donor, was recorded.

In conclusion, from said tests it results that all the NO donors according to the present invention, after incubation with endothelial cells or platelets for 5 minutes, are capable to generate NO, and to activate the cGMP synthesis in a concentration-dependent way, as determined by the utilized specific tests.

The following examples are given for illustrative purpose but are not limitative of the present invention.

EXAMPLES

Experimental Studies on Combinations Based on Potentially Toxic Drugs and on No Donors (Indicated by DON-NO)

A) Animals Studies

1) Study of the Renal Functionality After Administration of Anti-Tumoral Compounds (Cisplatin):

Sprague-Dawley male rats were daily treated with vehicle (physiologic saline solution, 0.9% sodium chloride, intraperitoneal (i.p.)) or cisplatin (i.p.) (5 mg/kg). Some animals received a daily dose of a NO donor, sodium nitroprussiate 0.2–1 mg/kg subcutaneous (s.c.). After five days the animals were sacrificed and the plasmatic urea and the plasmatic concentration of creatinine were determined. The data were analysed according to the bio-statistic methods commonly used.

As shown in Table 1, it resulted that the rats treated with cisplatin only showed meaningfully high levels of plastmatic urea and of creatinine, with respect to the control values (group receiving only the vehicle)

On the contrary, in animals, to which cisplatin and NO donor were administered, the biochemical parameters did not result meaningfully different from the control values.

2) Study of the Renal Functionality After Administration of Immuno-Depressive Compounds (Cyclosporin):

Sprague-Dawley male rats were daily treated with vehicle (physiologic saline solution, 0.9% sodium chloride, i.p.) or intraperitoneal cyclosporin (5 mg/kg i.p.). Some animals received a daily dose of a NO donor, sodium nitroprussiate 0.2–1 mg/kg s.c. After eighteen days the animals were sacrificed and the plasmatic concentration of creatinine and the activity of N-acetyl-beta D-glycosaminidase (NAG) in the urines were measured. The data were analysed according to the bio-statistic methods commonly used.

As shown in Table 2, it resulted that the rats treated with cyclosporin only showed meaningfully high levels of blood creatinine and of above urine NAG with respect to the control values (group receiving only the vehicle).

On the contrary, in animals, to which cyclosporin and DON-NO donor were administered, the biochemical parameters did not result meaningfully different from the control values.

3) Study of the Renal Functionality After Administration of Anti-Viral Compounds (Acyclovir):

Sprague-Dawley male rats were treated with vehicle (physiologic saline solution, 0.9% sodium chloride, i.p. a day) or intraperitoneal acyclovir (150 mg/kg i.p. a day). Some animals received a daily dose of a DON-NO (nitroglycerine 1–10 mg/kg s.c. a day). After fifteen days the animals were sacrificed and the plasmatic concentration of creatinine was determined. The data were analysed according to the conventional bio-statistic methods commonly used.

As shown in Table 1, it resulted that the rats treated with only acyclovir showed meaningfully high levels of blood creatinine with respect to the control values (group receiving only the vehicle).

On the contrary, in animals, to which acyclovir and DON-NO were administered, the biochemical parameters did not result meaningfully different from the control values (group receiving only the vehicle).

4) Study of the Renal Functionality and of the Gastrointestinal Tolerability in Arthritic Rats After Administration of Non-Steroidal Anti-Inflammatory Compounds (Ibuprofen, Naproxen, Indomethacin, Diclofenac) or Anti-Thrombotics (Aspirin):

Sprague-Dawley female rats were rendered arthritic, by an intracaudal injection of butyric Micobacterium inactivated by heat (0.6 ml suspended in 0.1 ml of mineral oil). After eighteen days, when the arthritic pathology was fully developed, the animals were daily treated with the vehicle (physiologic saline solution, 0.9% sodium chloride, i.p. a day) or NSAID [ibuprofen (60 mg/kg i.p. a day); indomethacin (10 mg/kg/i.p. a day); diclofenac (12 mg/kg i.p. a day; or naproxen (12 mg/kg i.p. a day)] or aspirin (250 mg/kg i.p. a day). Some animals received a daily dose of a DON-NO (sodium nitroprussiate 0.2–1 mg/kg s.c.; or nitroglycerin 1–10 mg/kg s.c. a day). After five days the animals were sacrificed and the plasmatic concentration of creatinine was determined. The data were analysed according to the conventional bio-statistic methods commonly used.

As shown in Table 3, it resulted that the rats treated with only NSAID or aspirin showed meaningfully high levels of blood creatinine with respect to the control values (group receiving only the vehicle); such animals showed also a marked pathology affecting the gastrointestinal apparatus, having a severity ranging from the mucous erosion to ulcer involving the muscular layer, intestinal adherences, abscites, peritonitis. In the other groups, treated with the vehicle or combining DON-NO plus NSAID or aspirin, the pathology was either of much smaller entity or even absent.

Moreover in the animals to which a NSAID or aspirin and a DON-NO were administered, the biochemical parameter did not result significantly different from the control values.

5) Study of the Renal Functionality and of the Gastrointestinal Tolerability in Hypertensive Rats, After Administration of Non-Steroidal Anti-Inflammatory Compounds (Diclofenac):

Sprague-Dawley male rats, spontaneously hypertensive (with systolic pressure variable between 180–220 mmHg) were daily treated with the vehicle (physiologic saline solution, 0.9 sodium chloride, i.p.) or NSAID[diclofenac (12 mg/kg i.p.)]. Some animals received a daily dose of an organic nitrate (nitroglycerin 1–10 mg/kg s.c. a day). After five days the animals were sacrificed and the plasmatic concentration of creatinine was determined. The data were analysed according to the conventional bio-statistic methods commonly used.

As shown in Table 4, it resulted that the rats treated with NSAID only showed meaningfully high levels of blood creatinine with respect to the control values (group receiving only the vehicle); such animals showed at the postmortem examination also a marked pathology affecting the gastrointestinal apparatus, of severity variable from the mucous erosion to ulcer involving the muscular layer, intestinal adherences, abscites, peritonitis. In the other groups, treated with the vehicle or combining DON-NO plus NSAID, the pathological picture affecting the gastrointestinal apparatus was either of much smaller entity or even absent.

Moreover in the animals to which diclofenac and DON-NO were administered, the biochemical parameter did not result significantly different from the control values.

6) Study of the Gastrointestinal Toxicity After Administration of Steroidal Anti-Inflammatory Compounds (Methylprednisolone):

Sprague-Dawley male rats were daily treated with the vehicle (physiologic saline solution, 0.9 sodium chloride, i.p.) or intraperitoneal methylprednisolone (5–10 mg/kg i.p.).

Some animals received a daily dose of a DON-NO (sodium nitroprussiate 0.2–1 mg/kg s.c.). After eighteen days the animals were sacrificed.

At the postmortem examination it resulted (Tab. 5) that such rats showed a marked pathology affecting the gastrointestinal apparatus, of severity variable from the mucous erosion to ulcer involving the muscular layer, intestinal adherences, abscites, peritonitis. In the other groups, treated with the vehicle only or with the combination nitrate plus steroid, the pathology was either of much smaller entity or even absent.

7) Study of the Effects of Nitroxybutylnaproxen (No-Naproxen) on Capsaicin Induced Bronchoconstriction in Enalapril-Treated Guinea Pigs Capsaicin-induced bronchoconstriction in guinea pigs is an animal model related to the ability of angiotensin-converting-enzyme inhibitors to provoke cough in patients (Subissi et al, J. Cardiovasc. Pharmacol. 20/1, 139–146, 1992).

NO-naproxen (2-(6-methoxy-2-naphthyl)propionate of 4-hydroxy-butyl) was synthetized according to Ex. 1, formula V) of International patent WO 95/09831.

Experimental conditions were as previously described by Del Soldato et al (J. Pharmacological Methods 5, 279, 1981). Female guinea pigs weighing 300–400 g were anesthetized through intraperitoneal injection of sodiun 5,5 diethylbarbiturate (200 mg/kg) and kept under artificial respiration at constant positive pressure. Jugular right vein was incannuled for the administration of the compounds. Animals received intraduodenally enalapril (10 mg/kg), vehicle (carboxymethyl cellulose 2% by weight) and/or NO-naproxen (10 mg/kg). Forty-five minutes later, it was injected intravenously 0.1 ml capsaicin (1 µg/kg). Before and after capsaicin injection, tidal air changes were measured by means of modified Konzett apparatus connected to a polygraph amplifier.

Results were calculated as ratio of the responses obtained before and after the administration of each treatment, expressed as % of the vehicle (control) response and shown in Table 7.

As shown in Table 7, NO-naproxen was able to reduce capsaicin-induced bronchoconstriction in enalapril treated guinea pigs. Enalapril increased capsaicin-induced bronchoconstrictive response, when administered alone.

B) Study on Patients

Study of the Renal Functionality in Patients After Administration of Anti-Tumoral Drugs (Cisplatin).

In some patients, separately observed, and in uncontrolled studies was evaluated the acute effect of some drugs such as cisplatin, alone or in the presence of a nitroglycerin patch.

The mono-administration of intraperitoneal cisplatin (90 mg per $m^2$) to patients, which needed an antitumoral therapy, caused a significant increase of blood creatinine in the first 24 hours, with respect to the initial values.

As it results from Table 6, when the patients were submitted to daily co-treatment with the nitroglycerin patch approximately releasing 15 mg/24 hours of nitroglycerin when the patch came into contact with the skin, such increase was much more limited and however significantly not different from the initial values.

The data were analysed according to the conventional biostatistic methods commonly used.

TABLE 1

STUDY OF THE RENAL FUNCTIONALITY IN RATS, AFTER THE REPEATED TREATMENT WITH CISPLATIN OR ACYCLOVIR, IN THE PRESENCE OR NOT OF NO DONOR. THE DATA ARE EXPRESSED AS PERCENT VARIATION WITH RESPECT TO THE CONTROL VALUE (GROUP TREATED WITH ONLY THE VEHICLE).

| TREATMENT | BLOOD UREA | BLOOD CREATININE |
|---|---|---|
| VEHICLE | 100 | 100 |
| CISPLATIN | 683* | 245* |
| CISPLATIN + DON-NO | 142 | 120 |
| ACYCLOVIR | — | 208* |
| ACYCLOVIR + DON-NO | — | 104 |

*$P < 0.05$ with respect to the control values.

TABLE 2

STUDY OF THE RENAL FUNCTIONALITY IN ARTHRITIC RATS AFTER THE REPEATED TREATMENT WITH CYCLOSPORIN IN THE PRESENCE OR NOT OF A DON-NO. THE DATA ARE EXPRESSED AS PERCENT VARIATION WITH RESPECT TO THE CONTROL VALUE (GROUP TREATED WITH ONLY THE VEHICLE)

| TREATMENT | NAG | BLOOD CREATININE |
|---|---|---|
| VEHICLE | 100 | 100 |
| CYCLOSPORIN | 220* | 187* |
| CYCLOSPORIN + DON-NO | 85 | 110 |

*$P < 0.005$ with respect to the control values

TABLE 3

STUDY OF THE RENAL FUNCTIONALITY IN ARTHRITIC RATS AFTER THE REPEATED TREATMENT WITH SOME ANTI-INFLAMMATORY COMPOUNDS, IN THE PRESENCE OR NOT OF DON-NO. THE DATA ARE EXPRESSED AS PERCENT VARIATION WITH RESPECT TO THE CONTROL VALUES (GROUP TREATED WITH ONLY THE VEHICLE)

| TREATMENT | BLOOD CREATININE |
|---|---|
| VEHICLE | 100 |
| IBUPROFEN | 292* |
| IBUPROFEN + SODIUM NITROPRUSSIATE (0.5 mg/kg s.c.) | 123 |
| IBUPROFEN + NITROGLYCERIN (3 mg/kg s.c.) | 142 |
| INDOMETHACIN | 355* |
| INDOMETHACIN + SODIUM NITROPRUSSIATE (0.5 mg/kg s.c.) | 138 |
| INDOMETHACIN + NITROGLYCERIN (3 mg/kg s.c.) | 130 |
| DICLOFENAC | 371* |
| DICLOFENAC + NITROGLYCERIN (3 mg/kg s.c.) | 122 |
| NAPROXEN | 323* |
| NAPROXEN + NITROGLYCERIN (3 mg/kg s.c.) | 164 |
| ASPIRIN | 280* |
| ASPIRIN + NITROGLYCERIN (3 mg/kg s.c.) | 112 |

*$P < 0.05$ with respect to the control values

TABLE 4

STUDY OF THE RENAL FUNCTIONALITY IN HYPERTENSIVE RATS, AFTER THE REPEATED TREATMENT WITH DICLOFENAC, IN THE PRESENCE OR NOT OF DON-NO. THE DATA ARE EXPRESSED AS PERCENT VARIATION WITH RESPECT TO THE CONTROL VALUES (GROUP TREATED WITH ONLY THE VEHICLE)

| TREATMENT | BLOOD CREATININE |
|---|---|
| VEHICLE | 100 |
| DICLOFENAC | 287* |
| DICLOFENAC + NITROGLYCERIN (3 mg/kg s.c.) | 148 |

*$P < 0.05$ with respect to the control values

TABLE 5

STUDY OF THE GASTROINTESTINAL TOLERABILITY IN RATS, AFTER THE REPEATED TREATMENT WITH METHYLPREDNISOLONE, IN THE PRESENCE OR NOT OF A DON-NO. THE SEVERITY DEGREE OF THE GASTRO-INTESTINAL PATHOLOGY WAS EVALUATED ACCORDING TO THE USUAL METHODS AND EXPRESSED IN ARBITRARY VALUES. THE DATA ARE EXPRESSED AS PERCENT VARIATION WITH RESPECT TO THE CONTROL VALUES (GROUP TREATED WITH ONLY THE VEHICLE)

| TREATMENT | GASTROINTESTINAL HARM |
|---|---|
| VEHICLE | 100 |
| PREDNISOLONE | 683* |
| PREDNISOLONE + SODIUM NITROPRUSSIATE (0.5 mg/kg s.c.) | 142 |

*$P < 0.05$ with respect to the control values

TABLE 6

STUDY OF THE RENAL FUNCTIONALITY IN ONCOLOGIC PATIENTS, AFTER THE TREATMENT WITH CISPLATIN, IN THE PRESENCE OR NOT OF A DON-NO. THE DATA ARE EXPRESSED AS PERCENT VARIATION WITH RESPECT TO THE INITIAL VALUES.

| | BLOOD CREATININE VALUES | |
|---|---|---|
| TREATMENT | INITIAL | FINAL |
| CISPLATIN | 100 | 183* |
| CISPLATIN + NITROGLYCERIN PATCH | 100 | 109 |

*$P < 0.05$ with respect to the control values.

TABLE 7

EFFECTS ON NITROXYBUTYLNAPROXEN (NO-NAPROXEN) ON CAPSAICIN INDUCED BRONCHOCONSTRICTION IN ENALAPRIL-TREATED GUINEA PIGS

| TREATMENT | BRONCHOCONSTRICTION (%) |
|---|---|
| VEHICHLE | 100 |
| ENALAPRIL | 290 |
| ENALAPRIL + NO-NAPROXEN | 20 |

What is claimed is:

1. A method of reducing at least one of gastrointestinal toxicity, renal toxicity or respiratory toxicity in a patient taking a non-nitroderivative drug selected from the group consisting of the following therapeutic classes: antitumoral other than cisplatin, immunodepressive, antiviral drugs, steroidal antiinflammatory agents, antibiotics, beta-adrenergic antagonists, and enalapril, the method comprising simultaneously, successively or previously administering to the patient an organic compound containing an —ONO$_2$ group, or an inorganic compound containing an —NO group, wherein the organic or inorganic compound releases NO and activates cGMP synthesis when the organic or inorganic compound is incubated in vitro with vasal endothelium cells or platelets for 5 minutes at a temperature of 37° C., the nitroderivative compounds being administered orally, transdermally or parenterally, wherein the organic compound containing an —ONO$_2$ group or the inorganic compound containing an —NO group is administered in an amount sufficient to reduce at least one of gastrointestinal toxicity, renal toxicity or respiratory toxicity, and the non-nitroderivative drug is not a NSAID.

2. The method according to claim 1, wherein the organic compound is selected from the group consisting of: clonitrate (3-chloro-1, 2-propanediol dinitrate), erythrityltetranitrate (1, 2, 3, 4 butanetetroltetranitrate), mannitol hexanitrate, nicorandil (N-[2-(nitrooxy)ethyl]-3-pyridine-carboxamide), nitroglycerin (1, 2, 3 propanetriol trinitrate), pentaerythritoltetranitrate (2,2,-bis [(nitrooxy)-methyl]-1,3-propanedioldinitrate), pentrinitrol (2,2-bis[(nitrooxy)methyl]-1,3-propane-diolmononitrate), propatylnitrate (2-ethyl-2-[(nitrooxy)methyl]-1,3-propanedioldinitrate), and trolnitratephosphate (2,2',2"-nitryltrisethanoltrinitrate phosphate) (salt 1:2).

3. The method according to claim 1 wherein the inorganic compound is a nitroprussiate.

4. The method according to claim 1, wherein the inorganic compound is sodium nitroprussiate (pentakis (cyano-C)nitrosylferrate(2)di-sodium).

5. The method according to claim 1, wherein the non-nitroderivative drug is selected from the group consisting of
5-fluorouracil;
cyclosporin;
acyclovir;
a steroidal anti-inflammatory drug selected from the group consisting of cortisone, dexamethasone and methylprednisolone;
an antibiotic selected from the group consisting of ciprofloxacin and gentamicine; enalapril; and
a beta-adrenergic antagonist selected from the group consisting of atenolol, metoprolol, timolol and propranolol.

6. The method according to claim 1, wherein the non-nitroderivative drug is selected from the group consisting of cyclosporin, dexamethasone and methylprednisolone.

7. The method according to claim 1, wherein when the nitroderivative compound is administered transdermically, a patch or plaster is used.

8. The method according to claim 7, wherein the patch is based on nitroglycerine.

9. The method of claim 1, wherein the organic or inorganic compound is administered at a dose that does not produce hypotension in the patient.

10. A pharmaceutical composition comprising:
a) a non-nitroderivative drug selected from the group consisting of the following therapeutic classes:
antitumoral other than cisplatin, immunodepressive, antiviral drugs, steroidal antiinflammatory agents, antibiotics, beta-adrenergic antagonists, and enalapril, and
b) an organic compound containing an —ONO$_2$ group or an inorganic compound containing an —NO group, wherein the organic or inorganic compound releases NO and activates cGMP synthesis when the organic or inorganic compound is incubated in vitro with vasal endothelial cells or platelets for 5 minutes at temperatures of 37° C.,
wherein the organic compound containing an —ONO$_2$ group or the inorganic compound containing an —NO group is present in an amount sufficient to reduce at least one of gastrointestinal toxicity, renal toxicity or respiratory toxicity.

11. A pharmaceutical composition comprising a non-nitroderivative drug which is cisplatin and an inorganic compound containing an —NO group, wherein the inorganic compound releases NO and activates cGMP synthesis when the inorganic compound is incubated in vitro with vasal endothelium cells or platelets for 5 minutes at a temperature of 37° C.

12. A method of reducing at least one of gastrointestinal toxicity, renal toxicity or respiratory toxicity in a patient taking a non-nitroderivative drug which is cisplatin,
the method comprising simultaneously, successively or previously administering to the patient an organic compound containing an —ONO$_2$ group, or an inorganic compound containing an —NO group, wherein the organic or inorganic compound releases NO and activates cGMP synthesis when the organic or inorganic compound is incubated in vitro with vasal endothelium cells or platelets for 5 minutes at a temperature of 37° C., the nitroderivative compounds being administered orally or parenterally,
wherein the organic compound containing an —ONO$_2$ group or the inorganic compound containing an —NO group is administered in an amount sufficient to reduce at least one of gastrointestinal toxicity, renal toxicity or respiratory toxicity.

13. A method of reducing at least one of gastrointestinal toxicity, renal toxicity or respiratory toxicity in a patient taking a non-nitroderivative drug selected from the group consisting of the following therapeutic classes: antitumoral other than cisplatin, immunodepressive, antiviral drugs, steroidal antiinflammatory agents, antibiotics, beta-adrenergic antagonists, and inhibitors of angiotensin converting enzyme,
the method comprising simultaneously, successively or previously administering to the patient an organic compound containing an —ONO$_2$ group, or an inorganic compound containing an —NO group, wherein the organic or inorganic compound releases NO and activates cGMP synthesis when the organic or inorganic compound is incubated in vitro with vasal endothelium cells or platelets for 5 minutes at a temperature of 37° C., the nitroderivative compounds being administered orally, transdermally or parenterally,
wherein the organic compound containing an —ONO$_2$ group or the inorganic compound containing an —NO group is administered in an amount sufficient to reduce at least one of gastrointestinal toxicity, renal toxicity or respiratory toxicity, and the non-nitroderivative drug is not a NSAID,
wherein the inorganic compound is a nitroprussiate.

14. A method of reducing at least one of gastrointestinal toxicity, renal toxicity or respiratory toxicity in a patient taking a non-nitroderivative drug selected from the group consisting of the following therapeutic classes: antitumoral other than cisplatin, immunodepressive, antiviral drugs, steroidal antiinflammatory agents, antibiotics, beta-adrenergic antagonists, and inhibitors of angiotensin converting enzyme,
the method comprising simultaneously, successively or previously administering to the patient an organic compound containing an —ONO$_2$ group, or an inorganic compound containing an —NO group, wherein the organic or inorganic compound releases NO and activates cGMP synthesis when the organic or inorganic compound is incubated in vitro with vasal endothelium cells or platelets for 5 minutes at a temperature of 37° C., the nitroderivative compounds being administered orally, transdermally or parenterally, wherein the organic compound containing an —ONO$_2$ group or the inorganic compound containing an —NO group is administered in an amount sufficient to reduce at least one of gastrointestinal toxicity, renal toxicity or respiratory toxicity, and the non-nitroderivative drug is not a NSAID, and wherein the inorganic compound is sodium nitroprussiate (pentakis (cyano-C)nitrosylferrate (2)di-sodium).

15. A method of reducing at least one of gastrointestinal toxicity, renal toxicity or respiratory toxicity in a patient taking a non-nitroderivative drug selected from the group consisting of the following therapeutic classes: immunodepressive, and steroidal antiinflammatory agents, the method comprising simultaneously, successively or previously administering to the patient an organic compound containing an —ONO$_2$ group, or an inorganic compound containing an —NO group, wherein the organic or inorganic compound releases NO and activates cGMP synthesis when the organic or inorganic compound is incubated in vitro with vasal endothelium cells or platelets for 5 minutes at a temperature of 37° C., the nitroderivative compounds being administered orally, transdermally or parenterally, wherein the organic compound containing an —ONO$_2$ group or the inorganic compound containing an NO group is administered in an amount sufficient to reduce at least one of gastrointestinal toxicity, renal toxicity or respiratory toxicity, and the non-nitroderivative drug is not a NSAID, and wherein the non-nitroderivative drug is selected from the group consisting of cyclosporin, dexamethasone and methylprednisolone.

16. A method of reducing at least one of gastrointestinal toxicity, renal toxicity or respiratory toxicity in a patient taking a non-nitroderivative drug selected from the group consisting of the following therapeutic classes: non-steroidal anti-inflammatory or anti-thrombotic;

the method comprising simultaneously or successively administering to the patient an organic compound containing an —ONO$_2$ group, wherein the organic compound releases NO and activates cGMP synthesis when the organic compound is incubated in vitro with vasal endothelium cells or platelets for 5 minutes at a temperature of 37° C., the nitroderivative compounds being administered orally, transdermally or parenterally, wherein the organic compound containing an —ONO$_2$ group is administered in an amount sufficient to reduce at least one of gastrointestinal toxicity, renal toxicity or respiratory toxicity, and wherein the anti-thrombotic drug is aspirin.

* * * * *